United States Patent [19]

Gergely et al.

[11] Patent Number: 5,323,413
[45] Date of Patent: Jun. 21, 1994

[54] APPARATUS FOR THE LASER DISSOCIATION OF MOLECULES

[75] Inventors: John S. Gergely, Ponca City, Okla.; Terry O. Trask, Midlothian, Va.; Samir A. Ahmed, New York, N.Y.

[73] Assignee: Conoco Inc., Ponca City, Okla.

[21] Appl. No.: 72,671

[22] Filed: Jun. 9, 1993

Related U.S. Application Data

[63] Continuation of Ser. No. 626,118, Dec. 11, 1990, abandoned.

[51] Int. Cl.⁵ .............................................. H01S 3/213
[52] U.S. Cl. ........................................ 372/53; 372/89; 372/99; 372/107; 204/157.4
[58] Field of Search ...................... 204/157.21, 157.22; 372/53, 55, 58, 85, 89, 99, 103, 107

[56] References Cited

U.S. PATENT DOCUMENTS

| | | | |
|---|---|---|---|
| 4,025,790 | 5/1977 | Jetter et al. | 204/157.22 |
| 4,124,466 | 11/1978 | Morrey | 204/157.1 |
| 4,272,681 | 6/1981 | Fill et al. | 204/157.22 |
| 4,360,923 | 11/1982 | Thayer, III et al. | 372/89 |
| 4,488,311 | 12/1984 | Davis et al. | 372/89 |
| 4,661,221 | 4/1987 | Robinson et al. | 204/157.22 |

OTHER PUBLICATIONS

Rabek, "Experimental Methods in Photochemistry & Photophysics", Part 2, Wiley & Sons, Sect. 16.3.7, p. 625.

Primary Examiner—W. Gary Jones
Assistant Examiner—Dean T. Nguyen
Attorney, Agent, or Firm—Cary A. Levitt

[57] ABSTRACT

An apparatus for dissociation of gas molecules which absorb light comprising a resonance optical cavity, a nozzle for introducing gas molecules into the resonance optical cavity in contact with the high velocity gas molecules, a focusing lens for focusing the laser beam at the point of contact of the laser beam and the high velocity gas molecules, a 100 percent reflecting mirror for receiving the laser beam after it passes through such molecules, a partially reflecting mirror positioned between the molecules for reflecting a portion of laser beam back into the laser and the remainder of the beam through the gas molecules to the 100 percent reflecting mirror.

1 Claim, 3 Drawing Sheets

APPARATUS FOR THE LASER DISSOCIATION OF MOLECULES

This is a continuation of application Ser. No. 07/626,118 filed Dec. 11, 1990, now abandoned.

BACKGROUND OF THE INVENTION

In the conventional method of producing tetrafluoroethylene (TFE) chlorodifluoromethane is subjected to elevated temperatures in the order of 700° to 800° C. At this temperature, the reactants thermally dissociate into TFE and other products. It is necessary to cool the reaction products to subzero temperatures in order to effect separation and recovery of the TFE. The energy cost of the commercial process is very high because of the large amounts of heat required and the necessity of reducing the reaction products to very low temperatures.

Multi photon dissociation (MPD) of molecules which absorb light through the use of lasers has been used by many investigators, primarily for isotope enrichment. MPD has also been used to dissociate reactants into various products, however, this method has not found commercial acceptance because of the low efficiency of the dissociation process.

Trifluoromethane ($CHF_3$) dissociates according to the following reaction steps:

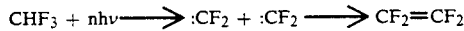

The overall efficiency of the conversion of $CHF_3$ with MPD to TFE is on the order of 0.03 to 0.12 percent. This efficiency is determined by multiplying together the three separate efficiencies which make up the MPD process; viz. pulsed laser wall plug efficiency, 3.0 percent; fractional absorbance of light by the reactant, 10–20 percent; and photon efficiency less than 100%, the energy required to break the chemical bonds of TFE produced divided by the total energy absorbed.

The low overall efficiencies of the MPD process have prevented the use of MPD for large scale commercial production of products such as TFE.

Use of the MPD process for the conversion of $CHF_3$ to TFE would provide substantial energy advantage over the conventional chemical process. The laser method does not require heat input because dissociation occurs by selective absorption of laser light rather than by heating. Cooling to separate products in the MPD process is required, but, the energy consumption is less than in the conventional chemical process because the products are obtained at a much lower temperature.

It is desirable to provide an MPD process and apparatus in which the efficiency of the dissociation of molecules to form desired products is substantially increased.

THE INVENTION

According to the process of the invention reactant molecules which absorb light are dissociated by introducing said molecules into a resonance optical zone in the form of a high velocity stream and contacting said stream of molecules in the resonance optical zone with a laser beam whereby said molecules are dissociated at a high reaction efficiency.

One aspect the invention is directed to apparatus for carrying out the above process in which the high velocity stream is provided by a nozzle and the resonance optical zone contains a plurality of reflecting means for reflecting the laser beam repeatedly through the high velocity stream of reactant molecules.

PRIOR ART

U.S. Pat. No. 4,025,790 to Jetter et al. relates to a process for separating the isotopes of a multi-isotopic element by forming a gas of isotopic compounds of the element, selectively exciting the molecules of one isotopic compound utilizing laser radiation, and separating the excited molecules from the other compounds. The separation step can be accomplished by either physical or chemical means. The efficiency of separating the compounds is improved by passing the gas through a nozzle causing it to undergo adiabatic expansion to form an undercooled supersonic gas stream prior to laser excitation followed by radiating the gas stream with a laser.

U.S. Pat. No. 4,272,681 to Fill et al. discloses a method and apparatus for separating Uranium isotopes using an iodine laser and an optical resonator.

U.S. Pat. No. 4,690,742 to Cantrell III et al. relates to a method and apparatus for laser isotope separation of atoms and molecules. The method consists of separating a selected isotope from a sample material comprising irradiating the sample with a first laser beam for producing an adiabatic population inversion of said selected isotope at an excited state. Then, the isotope is irradiated while in said selected isotope from said excited state. The apparatus contains gas, which includes a mixture of isotopes to be separated or enriched. The lasers used in the process are tunable.

U.S. Pat. No. 4,661,221 to Robinson et al. discloses a process for separating isotopes by selective excitation of isotopic species of a volatile compound utilizing tuned laser light. A highly cooled gas of the volatile compound is produced in which the isotopic shift is sharpened and defined. Before substantial condensation occurs, the cooled gas is irradiated with laser light precisely tuned to the desired wave length of selectively excite a particular isotopic species in the cooled gas. The adiabatic expansion of the gas is readily accomplished by means of contoured supersonic nozzles. The laser light imparts sufficient energy to the excited species in the gas to cause them to undergo a photochemical reaction or to photoionize.

"Megawatt Infrared Laser Chemistry of $CCLF_3$ and $CCL_3F$, Photochemistry, Photophysics, and Effect of $H_2$," David F. Dever and Ernest Grunwald, *Journal Of The American Chemical Society*; volume 98, No. 17, Aug. 18, 1976, Pages 5055 through 5062. This reference relates to a process for converting $CCLF_3$ and/or $CCL_3F$ to reaction products using a tunable pulsed $CO_2$ laser and hydrogen gas. The addition of hydrogen to the reactants is said to increase the reaction rate and modify the products.

K. Takeuchi, I. Inoue, R. Makane, Y. Makide, S. Kato, and T. Tominaga, $CO_2$ Laser Tritium Isotope Separation: Collisional Effects in Multiphoton Dissociation of Trifluoromethane", Journal of Chemical Physics, Volume 76, No. 1, Jan. 1, 1982, pp. 398 to 405.

DETAILED DESCRIPTION OF THE INVENTION

Figure 1:
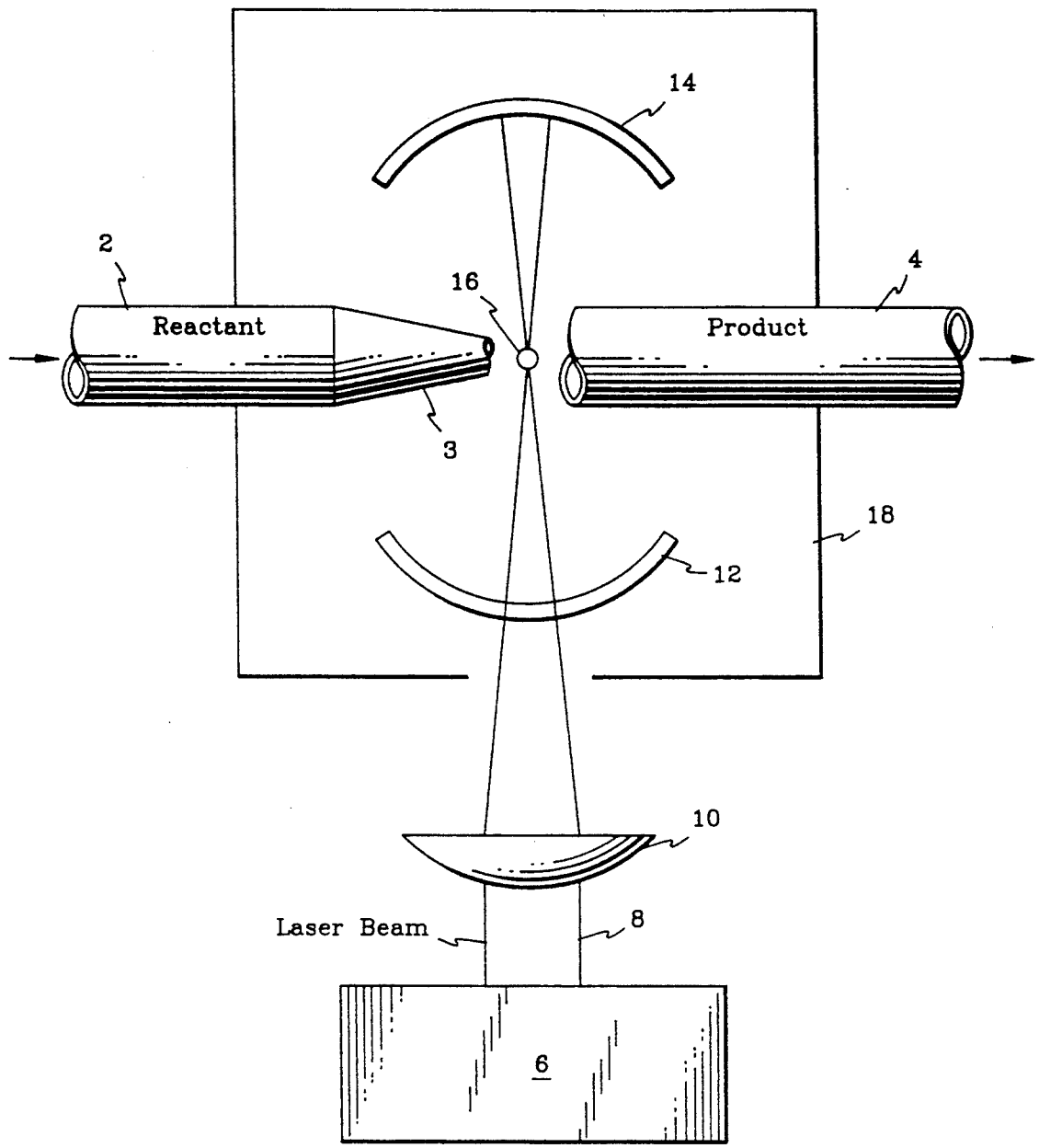
FIG. 1 is a schematic diagram of apparatus used in carrying out the invention.

The process of the invention in one aspect may be described by reference to FIG. 1. Referring to FIG. 1, a stream of reactant gas molecules which absorb light is introduced to a resonance optical zone 18 through line 2. The reactant gas passes through nozzle 3 from which it exits as a high velocity stream. A laser source 6 is provided which emits a high energy laser beam 8. This beam passes through a focusing lens or optical integrator 10 to concentrate the laser light at the exit of the nozzle at point 16 where it intersects the high velocity reactant gas. A portion of the light contained in the laser beam is absorbed by the reactant gas as the laser beam passes through the flowing stream of gas. Unabsorbed light contained in the laser beam expands in cross section and contacts a 100 percent reflecting mirror 14 which refocuses the laser beam and returns it back to point 16 where it again intersects the flowing reactant gas. Positioned between point 16 and focusing lens 10 is a partially reflecting mirror 12. The main purpose of mirror 12 is to increase the intensity of light circulating in resonance optical zone 18. Light reflected off mirror 14 which is not absorbed by the reactant gas at point 16 strikes mirror 12. Mirror 12 reflects a portion and transmits a portion of this light. The portion of light which is reflected is refocused back on itself and adds to the laser light that left the laser and was transmitted through mirror 12. These two quantities of light add constructively resulting in a greater field intensity within the resonance optical zone. The portion of light reflected off mirror 14, not absorbed by the reactant gas at point 16, and transmitted through mirror 12 enters the laser for reamplification. The reamplification process reduces unused light in the resonance optical zone because the light reenters the laser is reamplified and readmitted from the laser back into the resonance optical zone. Therefore, no unused light is lost from the process as would be the case in a single pass arrangement without a resonance optical zone. This arrangement in effect, increases the effective fractional absorbance to nearly 100% since all the light is used and none is lost.

The process of the invention is generally applicable to the dissociation of any gaseous molecule which absorbs light. Among the better known reactants are the organo-fluorides such as chlorodifluoromethane, trifluoromethane, tetrafluoroethylene, chlorotrifluoromethane, octafluorocyclobutane and the corresponding bromine substituted compounds. Many other compounds can be dissociated with a laser in accordance with the process of the invention. A few examples include the reaction of carbon dioxide and sulfur hexafluoride with a carbon dioxide laser to form carbonylfluoride, the dissociation of ethane, methane, or other paraffin hydrocarbons with an infrared laser to form acetylene and the dissociation of ethylene dichloride to vinyl chloride with an excimer laser.

A wide variety of lasers may be used in carrying out the process of the invention depending on the particular compounds which are to be dissociated. They include infrared lasers using various gases such as carbon dioxide, carbon monoxide, hydrogen fluoride, hydrogen chloride, carbon disulfide, iodine etc. Also useful are excimer lasers which operate in the ultraviolet light range. These lasers are pulse lasers with high energy per pulse and high power input. Also useful are dye lasers which operate in the ultraviolet to near infrared light spectrum. Such lasers are sold under the trade names such as Rhodamine 6G ® and Rhodamine B ®.

In carrying out the process of the invention, a reaction of particular interest is the dissociation of trifluoromethane to form tetrafluoroethylene utilizing a tunable $CO_2$ laser. This particular reaction is of interest for a number of reasons. As previously pointed out, the conventional chemical method of producing tetrafluoroethylene has the disadvantage of utilizing large amounts of energy since the reaction is carried out at a very high temperature. Cooling from this very high temperature is required to separate the products. The dissociation of trifluoromethane with MPD to form tetrafluoroethylene is carried out at low temperatures and thus does not require a major expenditure of heat energy and the associated cooling energy requirements. As another disadvantage, perfluroisobutylene which is a highly toxic material is obtained as a waste product in the high temperature commercial tetrafluoroethylene process. This material, of course, must be separated from the tetrafluoroethylene product and safely disposed of. The conversion of trifluoromethane to tetrafluoroethylene in accordance with the process of the invention does not produce any perfluoroisobutylene.

Figure 2:
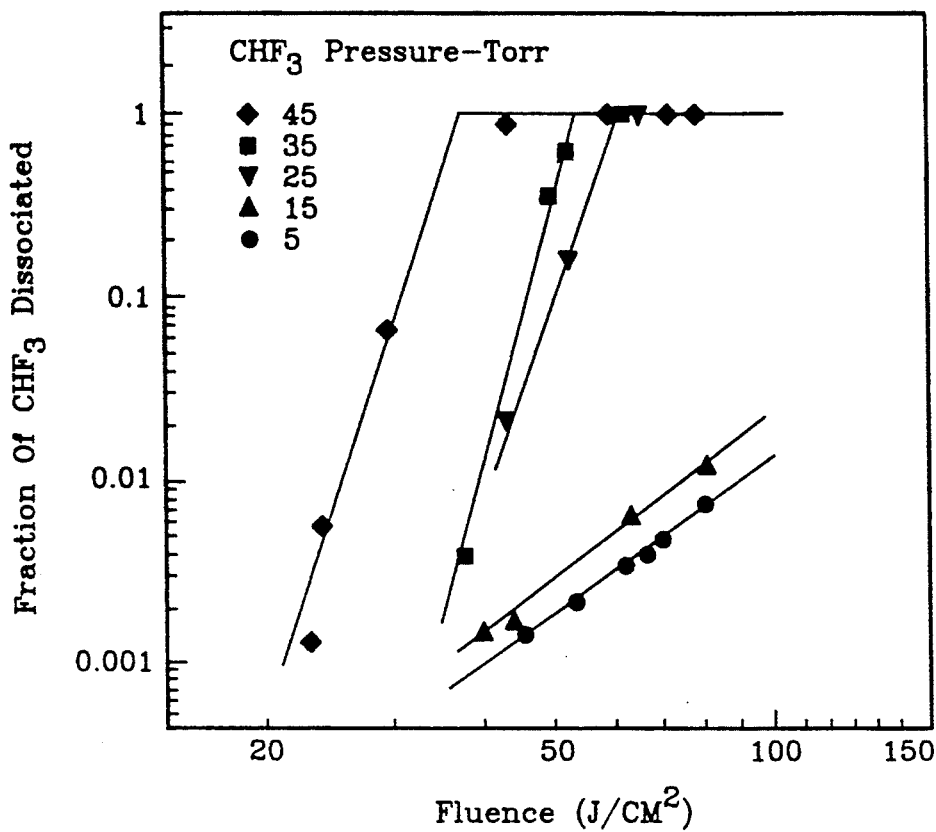
FIG. 2 is a plot of the fraction of $CHF_3$ dissociated versus fluence for several pressures of $CHF_3$.

One of the efficiencies of the MPD process previously referred to is the photon efficiency, i.e. the energy required to break the chemical bonds of the TFE produced divided by the total energy absorbed. It is desirable of course to have this particular efficiency as high as possible. During the course of studying the use of MPD for isotope enrichment, one investigator, Takeuchi, previously referred to, studied the enrichment of deuterium and tritium in trifluoromethane. Takeuchi of course was only interested in isotope separation and in order to obtain the desired selectivity, it was necessary for him to work at low pressures on the order of 5 to 45 torr. In his work, he studied the effect of increasing the reaction pressure on the system. He noted that as the reaction pressure increased, the energy density input decreased and the percent of trifluoromethane dissociated eventually reached 100 percent. The results of his study are presented in FIG. 2. Referring to this figure, it is noted that 100 percent dissociation of trifluoromethane was obtained at a pressure of 45 torr (millimeters of mercury) with an energy input of about 40 joules per square centimeter fluence. This value of the fluence, which is required to effect 100 percent conversion of the trifluoromethane is known as the critical fluence.

The trend shown by Takeuchi would be expected to continue above 45 torr, in fact, at atmospheric pressure (760 torr) the critical fluence may be as low as a single digit. Furthermore, Takeuchi did not use the optimum wavelength to dissociate trifluoromethane. He used the 1074.6 cm$^{-1}$ line from a $CO_2$ laser, which is far from the maximum trifluoromethane absorption, which is between 1100 to 1140 cm$^{-1}$. Tuning the $CO_2$ laser closer to the optimum wavelength would increase the absorption considerably and reduce the critical fluence.

The process of the invention may be carried out at higher pressures than those required for isotope separation without affecting the yields and selectivity of the products desired. This allows the process to be practiced near or at critical fluence, i.e., from about 90% to about 100% critical fluence, and thus ensures high photon efficiency and high throughput. For example, pressures up to as high as one atmosphere (760 torr) or higher may be employed. Usually, however, the pressure will be maintained between about 40 and about 700 torr.

The velocity of the reactant gas when it contacts the laser beam is controlled so that the reactant gas molecules receive sufficient energy to effect dissociation of the molecules. The velocity attained by the reactant gas is based on a number of factors including the area of the nozzle through which the gas is introduced in contact with the laser beam, the total laser power, the density of the reactant gas molecules in the interaction region and the activation energy of the reactant gas molecules.

The desired reactant gas velocity may be obtained from the following equation:

$$V = \frac{P}{nAE}$$

where
V = velocity of reactant gas in the interaction region-meters/sec
P = total laser power-watts
n = density of the reactant gas molecules in the interaction region-molecules/cm$^3$
A = area of nozzle opening-cm$^2$
E = activation energy of reactant gas molecules-K Joules/mole For example, when converting octofluorocyclobutane to TFE at a pressure of 140 Torr, with a laser power of 6 KW and using a nozzle opening of 0.16 cm$^2$ the velocity of the reactant gas in the interaction region is 147 meters/sec or Mach 0.42.

In carrying out the process of the invention the velocity of the reactant gas may vary from as low as 80 meters/sec as to as high as Mach 4 or about 1400 meters/sec. Thus, the velocity may be less than or greater than the speed of sound (Mach 1).

The photon efficiency attained in carrying out the process of the invention will vary with the particular feedstock employed. Usually, the photon efficiency will be at least 75% and preferably from about 90% to about 100%.

Another efficiency which makes up the total efficiency of the MPD process is the percent of laser light which is absorbed in the reaction cell. As pointed out previously, this efficiency for the conventional method is between 10 and 20 percent. On the other hand, using the arrangement shown in FIG. 1, any light which is not absorbed in the first pass through the reactant stream is absorbed by the molecules of gas through multiple reflections in the resonance optical zone. Through the use of this zone, it is possible to increase the efficiency of absorbance to a very high level, approaching 100 percent efficiency, because very little light is lost.

Referring again to FIG. 1, focusing lens 10 may be made of any material which is customarily used for this purpose such as germanium or zinc selenide. If a beam integrator is used to shape the beam generated at point 16 it may be made of gold-coated, water cooled copper. The 100 percent reflecting mirror 14 may be constructed with a gold plated face and a copper backing or if desired, the face may also be of polished copper. Since this mirror becomes heated during the process, it is usually cooled with a liquid such as water. The partially reflecting mirror may be made of germanium with the proper dielectric coating to give the required partially reflecting characteristics. This mirror is similar to CO$_2$ laser mirrors and is available from Interoptics Corp of Canada.

The reaction of trifluoromethane to produce tetrafluoroethylene is preferably carried out with a CO$_2$ laser which has been tuned near to the maximum absorbance frequency of the trifluoromethane. A pulsed laser may be used, however, a continuous laser system is preferred since the continuous lasers are more efficient than the pulsed lasers. A continuous laser may have a wall plug efficiency of as high as 10 to 12 percent as compared to the 3 to 7 percent wall plug efficiency of the pulsed laser.

All of the components of the apparatus of the invention are well known and are commercially available from a variety of sources. None of these components in themselves constitute a part of the invention.

Figure 3:
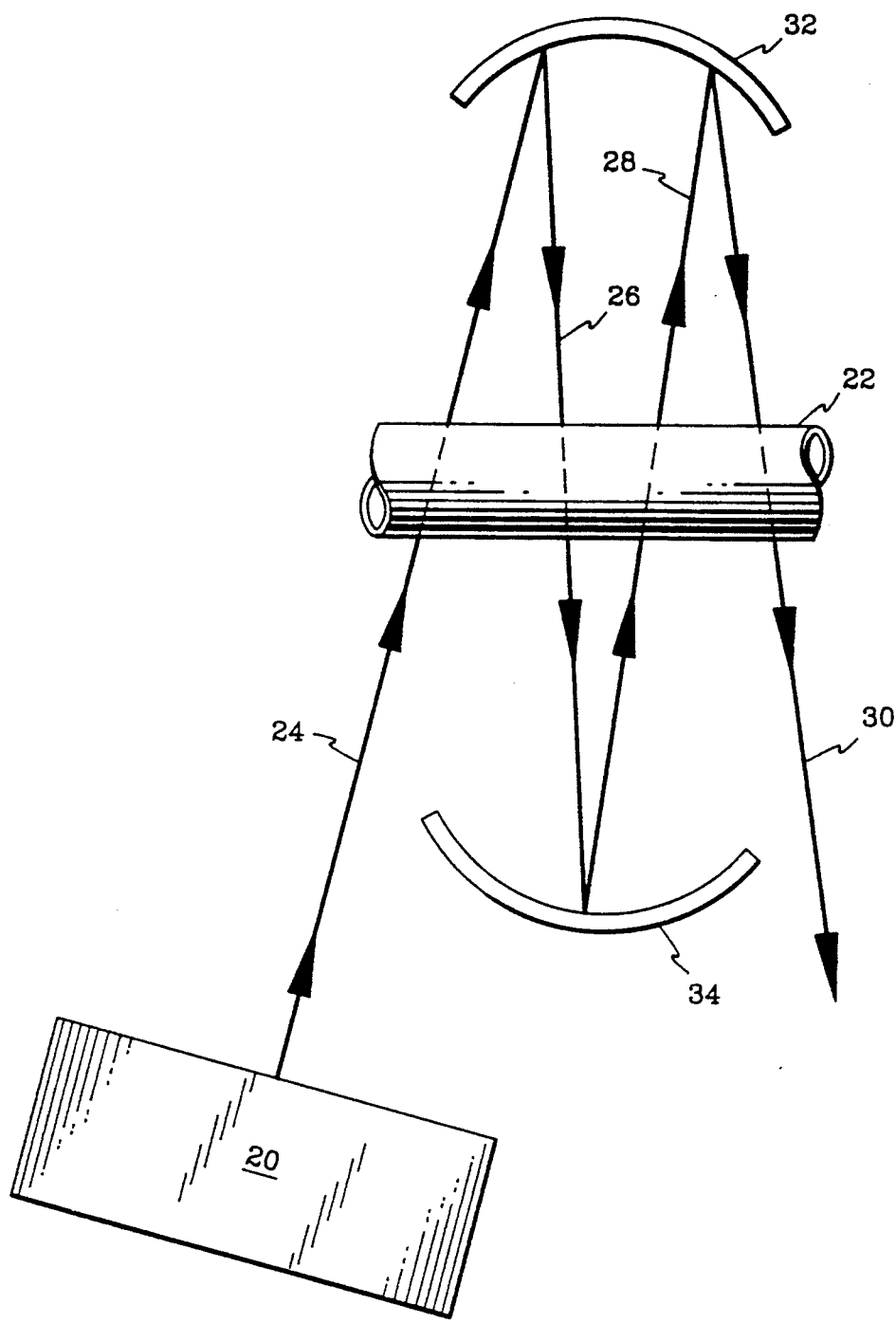
FIG. 3 represents another apparatus arrangement for carrying out the invention.

Another apparatus arrangement suitable for carrying out the process of the invention is shown in FIG. 3. In this Figure, 22 designates the high velocity stream of reactant gas molecules which is contacted by the laser beam. The laser beam which is provided from source 20 passes along path 24 through the reactant gas and contacts 100 percent reflecting mirror 32 which reflects the beam back along path 26 to 100 percent reflecting mirror 34. This mirror in turn reflects the laser beam along path 28 to mirror 32 where the beam is again reflected through the reactant gas along path 30. The reflecting mirrors 32 and 34 and additional mirrors if required can be positioned in such a manner to provide any desired number of passes of the laser beam through the flowing high velocity gas stream whereby essentially complete absorbance of light by the reactant gas is obtained. If desired, the mirrors may be adjusted to provide overlap of beams 24, 26, 28 and 30 in region 22.

The velocity required by the reactant gas in the interaction region depends on the cross section of the focused laser spot. It is possible to provide a focused laser spot of various sized cross sections. One of the ways in which enlargement of the focused laser spot may be effected is by the use of an optical integrator which contains a plurality of gold plated copper pyramids that reflect light. Thru the use of such an integrator, several of which are commercially available, the laser beam may be focused to provide a square or rectangular spot of considerably larger cross-section than would normally be obtained. Focused laser spots of 0.25 square millimeters, up to as much as 10 square centimeters or higher may be obtained in this manner.

Figure 4:
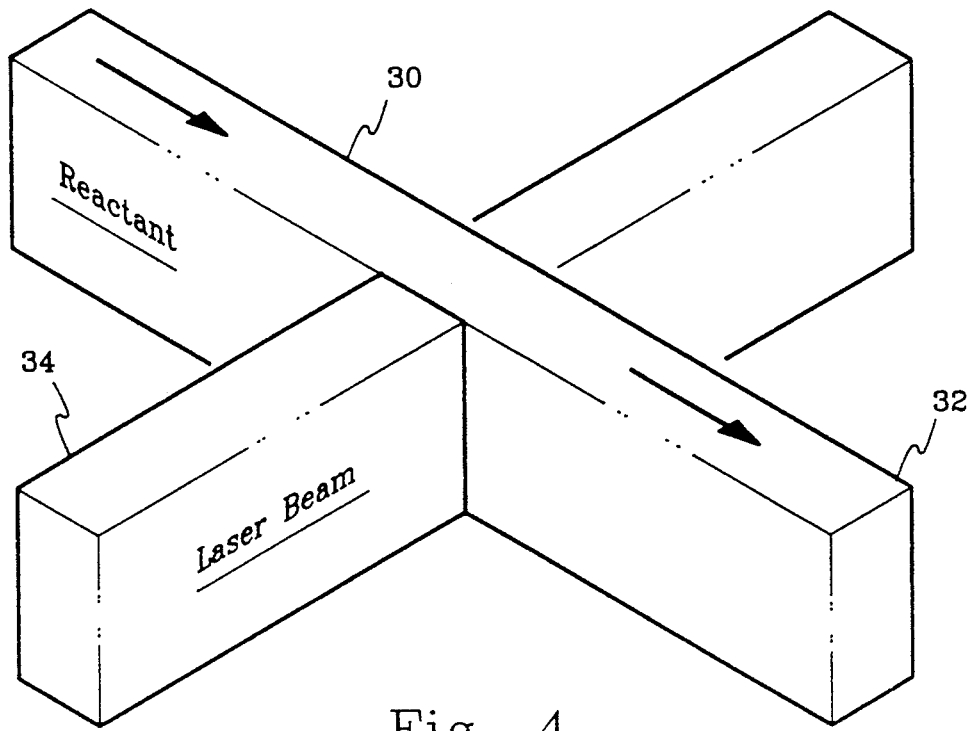
FIG. 4 is a schematic representation of a particular geometry for the reactor feed stream and laser beam used in the process and apparatus of the invention.

A typical rectangular focused laser spot is shown in FIG. 4 in which a reactant gas stream of rectangular cross section 30 is shown intersecting a laser beam 34 of equal rectangular cross section, with the reaction products leaving the reaction zone at 32. The cross section shown may have dimensions of 2 by 5 millimeters which would provide a focused laser spot of 10 square millimeters.

The flowing reactant stream 30, which has the same cross-section as the focused laser spot may be attained by the use of a nozzle having a rectangular cross section.

In contrast to its desirable properties, tetrafluoroethylene is a highly explosive material which must be shipped in admixture with hydrogen chloride to prevent explosion. Since tetrafluoroethylene is only manufactured at few locations, this means that extensive safety precautions must be taken in order to ship this material to the many locations around the country where it is used. Similar problems of course, are also encountered in the manufacture and shipment of tetrafluoroethylene in other countries.

By following the procedure previously described, the process of the invention can be used to dissociate the dimer of tetrafluoroethylene which is octafluorocyclobutane. When dissociated, this dimer forms tetrafluoroethylene. Octafluorocyclobutane is a stable material which may readily be transported from one location to another without undue safety concerns. The process of the invention can be readily utilized to dissociate octafluorocyclobutane at the numerous locations either close to or on site where the tetrafluoroethylene is to be used. This will of course, substantially reduce or obviate the problems inherent in transferring tetrafluoroethylene over long distances.

The preferred method of carrying out the process of the invention is with a continuous wave (CW) laser because of its higher wall plug efficiency and continuous produce throughput. However, the process will also work effectively with a pulsed laser. For the pulse mode of operation the flow rate of reactant from the nozzle must be adjusted to replace the reacted feed with new unreacted feed in the reaction region between laser pulses.

While certain embodiments and details have been shown for the purpose of illustrating the present invention, it will be apparent to those skilled in the art that various changes and modifications may be made herein without departing from the spirit or scope of the invention.

We claim:

1. Apparatus for dissociating gaseous molecules which absorb light comprising a) a resonance optical cavity, b) means for introducing gas molecules into the resonance optical cavity at a high velocity, c) means for introducing a laser beam into the resonance optical cavity in contact with high velocity gas molecules, and d) a plurality of reflecting means in the resonance optical cavity for reflecting the laser beam repeatedly through the high velocity gas molecules, e) at least one of said reflecting means comprising a 100 percent reflecting mirror for receiving the laser beam after it passes through the gas molecules and reflecting the laser beam back through said molecules and f) at least one of said reflecting means comprises a partially reflecting mirror, wherein the apparatus is configured such that the laser beam passes through the partially reflecting mirror prior to passing through the gas molecules and the partially reflecting mirror receives the laser beam after it has reflected from said 100 percent reflecting mirror and passed back through said molecules, and a portion of the laser beam is passed through said partially reflecting mirror and admitted back into the laser where the laser beam is reamplified and again passed into the resonance optical cavity.

* * * * *